(12) United States Patent
Zhou et al.

(10) Patent No.: US 7,650,190 B2
(45) Date of Patent: Jan. 19, 2010

(54) METHODS AND APPARATUS FOR THE REGULATION OF HORMONE RELEASE

(75) Inventors: Xiaohong Zhou, Plymouth, MN (US); Thomas J. Mullen, Ham Lake, MN (US); Gary W. King, Fridley, MN (US); Michael R. S. Hill, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 409 days.

(21) Appl. No.: 11/751,813

(22) Filed: May 22, 2007

(65) Prior Publication Data
US 2008/0140150 A1 Jun. 12, 2008

Related U.S. Application Data

(63) Continuation of application No. 10/426,610, filed on Apr. 30, 2003, now Pat. No. 7,221,979.

(51) Int. Cl.
*A61N 1/00* (2006.01)
(52) U.S. Cl. .................... 607/44; 607/2; 607/45
(58) Field of Classification Search ............ 607/1–3, 607/6, 9, 58, 59, 117, 118; 600/301, 309, 600/322
See application file for complete search history.

(56) References Cited

U.S. PATENT DOCUMENTS

| | | | |
|---|---|---|---|
| 4,146,029 A | 3/1979 | Ellinwood, Jr. | |
| 4,428,378 A | 1/1984 | Anderson et al. | |
| 4,903,701 A | 2/1990 | Moore et al. | |
| 5,058,584 A | 10/1991 | Bourgeois | |
| 5,220,917 A | 6/1993 | Cammilli et al. | |
| 5,292,336 A | 3/1994 | Spence, Jr. et al. | |
| 5,330,505 A | 7/1994 | Cohen | |
| 5,331,966 A | 7/1994 | Bennett et al. | |
| 5,464,434 A | 11/1995 | Alt | |
| 5,564,434 A | 10/1996 | Halperin et al. | |
| 5,607,418 A | 3/1997 | Arzbaecher | |
| 5,824,021 A | 10/1998 | Rise | |
| 6,058,331 A | 5/2000 | King | |
| 6,134,470 A | 10/2000 | Hartlaub | |
| 7,221,979 B2 | 5/2007 | Zhou et al. | |
| 2002/0107553 A1 | 8/2002 | Hill et al. | |
| 2002/0143369 A1 | 10/2002 | Hill et al. | |
| 2002/0165586 A1 | 11/2002 | Hill et al. | |
| 2003/0004549 A1 | 1/2003 | Hill et al. | |

*Primary Examiner*—Carl H Layno
*Assistant Examiner*—Yun Haeng Lee
(74) *Attorney, Agent, or Firm*—Stephen W. Bauer

(57) ABSTRACT

A method and apparatus for delivering corrective therapy through hormone regulation is provided. Inhibition of sympathetic fibers by spinal cord stimulation is used to regulate the levels of hormones such as catecholamines, renin, and calcitonin gene-related peptide. The invention utilizes a closed or open loop feedback system in which physiological parameters such as the concentrations of hormones and sympathetic indicators such as heart rate and urine production are monitored and used to determine the appropriate level of neurostimulation. The site of electrical stimulation includes, but is not limited to, the spinal cord at levels T7-L2 and the associated neural fibers within a region of the T7-L2 dermatomes.

20 Claims, 10 Drawing Sheets

METHODS AND APPARATUS FOR THE REGULATION OF HORMONE RELEASE

CROSS REFERENCE TO RELATED APPLICATION

This patent disclosure is a continuation of U.S. patent application Ser. No. 10/426,610 filed 30 Apr. 2003, which issued as U.S. Pat. No. 7,221,979 on 22 May 2007, the contents of which are incorporated herein by reference.

FIELD OF THE INVENTION

This invention relates generally to a method and apparatus for electrically stimulating select nerves to regulate hormone release, and more particularly, to sympathetic nerve modulation to regulate levels of hormones to ameliorate cardiovascular disease.

DESCRIPTION OF THE RELATED ART

Electrical stimulation of the spinal cord and other nerves has been used to treat various cardiac conditions such as cardiac arrhythmias, angina pectoris, ventricular dysfunction, heart failure and other cardiac conditions. Typically, electrodes are implanted in the patient adjacent the spinal area and electrically excited to produce desirable effects on the functioning of the heart. For example, Bilgutay et al., describe a system that delivers electrical stimulation to the vagus nerve using silastic coated, biopolar electrodes (Bilgutay et al., "Vagal Tuning," Journal of Thoracic and Cardiovascular Surgery, 56: 71-82 (1968)). In this system, a controlled current is delivered to nerves through electrodes that are surgically implanted in or around the intact nerves producing a decreased heart rate while preserving sinus rhythm.

A series of published U.S. patent applications, U.S. Published Application Nos. 20020165586 A, 20020143369 A1, 20020107553 A1, and 20030004549 A1, assigned to Medtronic, Inc. the assignee of the instant application, describe the use of electrical stimulation of the spinal cord to prevent and treat certain cardiac conditions. These applications describe systems that provide nerve stimulation in a manner designed to improve the cardiac performance and efficiency of a patient's heart.

In addition to the above-described systems, other systems have been described to provide nerve stimulation following the onset of a predetermined condition. For example, U.S. Pat. No. 6,134,470 to Hartlaub describes a system for utilizing spinal cord stimulation to terminate tachyarrhythmia after the tachyarrhythmia or a tachyarrhythmia precursor is detected.

Electrical stimulation delivered to the nervous system using an implanted electrode has been used effectively to relieve chest pain, such as angina pectoris, that sometimes accompanies myocardial ischemia. U.S. Pat. No. 5,058,584 to Bourgeois describes a system and method for treating chest pain using electrical stimulation within the epidural space of the spinal cord. Similarly, U.S. Pat. No. 6,058,331 to King discloses a system and method for treating ischemia by automatically adjusting electrical stimulation to the spinal cord, peripheral nerve, or neural tissue ganglia based on a sensed patient condition.

Certain cardiac conditions result from an imbalance in the neuro-endocrinological systems, including the sympathoadrenomedullary and the renin-angiotensin systems. These conditions are commonly treated with hormone-affecting drugs. In particular, understanding of the effect of the renin-angiotensin system (RAS) and the sympathetic nervous system (SNS) in the pathophysiology of cardiovascular problems has resulted in the development of a number of drugs, which manipulate these hormonal systems.

Blockade of the RAS with ACE inhibitors is currently a mainstay in the treatment of heart failure. In heart failure, there is an activation of the RAS resulting in sodium and fluid retention, which is harmful over time. ACE inhibitors are also used for the treatment of hypertension, myocardial infarction, and nephropathy.

Beta-adrenergic receptor blocking agents, also referred to as beta-blockers, have also been shown to have beneficial effects on the sympathetic nervous system in heart failure and post myocardial infarction. Beta-blockers compete with beta-adrenergic receptor stimulating agents for available beta-receptor sites, thereby decreasing the cardiac adrenergic activity, which results in arrhythmia and myocyte toxicity. In addition to beta-blockers, sympatholytic agents such as moxonidine, which reduces plasma catecholamine levels, have been investigated as cardiovascular agents.

Other cardiovascular agents targeting neurohormones include endothelin receptor antagonists, endothelin-converting-enzyme inhibitors, cytokine antagonists, vasopeptide inhibitors, inotropic agents, and agents augmenting natriuretic peptide. For a review of these various agents, see G. Wells and W. Little in "Current Treatment and Future Directions in Heart Failure," *Current Opinions in Pharmacology*, 2: 148-153 (2002).

Treating cardiovascular and other disorders through use of hormone-regulating drugs is not without problems. The dosages are patient dependent, and thus proper dosages must be determined on a patient-by-patient basis. Drugs may also have pharmacokinetic problems due to the difficulty of maintaining the proper dose in an individual over time. This is particularly true for drugs with a rapid onset and short duration of action. Effective treatment also depends on patient compliance with prescribed treatment dosages and schedules, which studies have shown occurs only 50-70% of the time in the case of hypertension medication. Additionally, many currently available drugs have notable side effects. For example, patients treated with beta blockers are at risk for fatigue, bradycardia, heart failure, insomnia, impaired peripheral circulation, and asthma, while aldosterone antagonists such as spironolactone affect estrogen and androgen receptors, resulting in unfavorable side effects such as gynecomastia. ACE inhibitors, through their effect on the RAS, may cause potassium retention and hyperkalaemia. They may also cause a persistent dry cough, renal and blood disorders, hypersensitivity reactions. They are also prone to causing significant hypotension, particularly for the first dose.

Thus, while hormone-affecting drugs have a diverse range of useful abilities, they are also burdened with inherent problems such as proper dosing, patient compliance, and side effects. What is needed is a method and apparatus for regulating the release of hormones, including cardiovascular hormones, by electrical stimulation, to treat a variety of conditions, without the attendant problems of existing hormone-regulating drug.

SUMMARY OF THE INVENTION

The present invention is useful for controlling electrical stimulation of neural tissue to regulate the release of hormones in a patient to modulate the hormone level and prevent hormone imbalances that result in physiological disorders such as certain cardiac conditions.

In one aspect of the instant invention, an apparatus is provided for controlling the electrical stimulation of the spinal cord or other neural tissue to modulate the release of one or more hormone. The apparatus includes one or more sensors, a controller, and one or more stimulation electrodes. The sensor detects one or more physiologic parameters of the patient that may indicate a hormone imbalance. The sensor may be external or implanted. The controller processes information received from the sensor and compares the value of a sensed physiologic parameter with values stored in the controller or to the value of one more other sensed physiologic parameters to determine if a hormone imbalance may exist. If the determination is made that the sensed value indicates an imbalance then the controller will generate a stimulation pulse having predetermined stimulation parameters. A stimulation electrode delivers the pulse to precise locations adjacent to the spinal cord or associated dermatomes associated with the release of a particular hormone to increase or decrease the release of that hormone. In alternative embodiments, the stimulation is provided to the spinal cord at levels T7-L2, neural fibers within a region of the T7-L2 dermatomes or in neural tissue nearest the kidneys or in neuronal ganglia. Release of the targeted hormone is either increased or decreased which will result in a change in the physiologic parameters being monitored.

In another aspect of the invention, an apparatus is provided for preventing or treating cardiac conditions. The method includes sensing or monitoring physiologic parameters associated with heart function, including, concentrations of certain cardiovascular hormones, such as catecholamines and renin, and sympathetic activity indicators, such as heart rate, QT interval, baroreflex sensitivity, blood pressure and urine production. When an imbalance or physiologic parameter measured indicates that a value is abnormally high or low for the patient then electrical stimulation is applied to neural tissue in the patient's body associated with the release of a cardiovascular hormone, such as a catecholamine or renin, to increase or decrease the release of the hormone.

BRIEF DESCRIPTION OF THE DRAWINGS

The above and other objects and aspects of the invention will be apparent from the description of embodiments illustrated by the following accompanying drawings:

FIG. 5 is a graph illustrating one method of determining value T1 used in the control routine of FIG. 4A.

DETAILED DESCRIPTION OF SPECIFIC EMBODIMENTS

Illustrative embodiments of the invention are described below. In the interest of clarity, not all features of an actual implementation are described in the specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of a method and apparatus for electrically regulating the release of hormones, including cardiovascular hormones, to treat a variety of conditions according to the present invention are shown in the Figures. As will be readily apparent to those skilled in the art upon a complete reading of the present application, the present method and apparatus are applicable to a variety of systems other than the embodiments illustrated herein.

Generally, the present invention is directed to a method and apparatus for regulating the release of hormones through electric stimulation. In the embodiments described herein, the aspect of electrically stimulating the spinal cord and associated dermatomes and other nerves to cause the regulation of hormones affecting the cardiovascular system is emphasized, but the present invention is not limited to this application. In the illustrated embodiments, the current invention uses electrical stimulation delivered by electrodes to inhibit signaling along sympathetic fibers originating from the spinal cord in order to innervate the kidneys and the adrenal medulla. In one embodiment, spinal vertebral levels T7-L2 and associated dermatomes are specifically stimulated, suppressing their associated sympathetic signals.

Figure 1A:
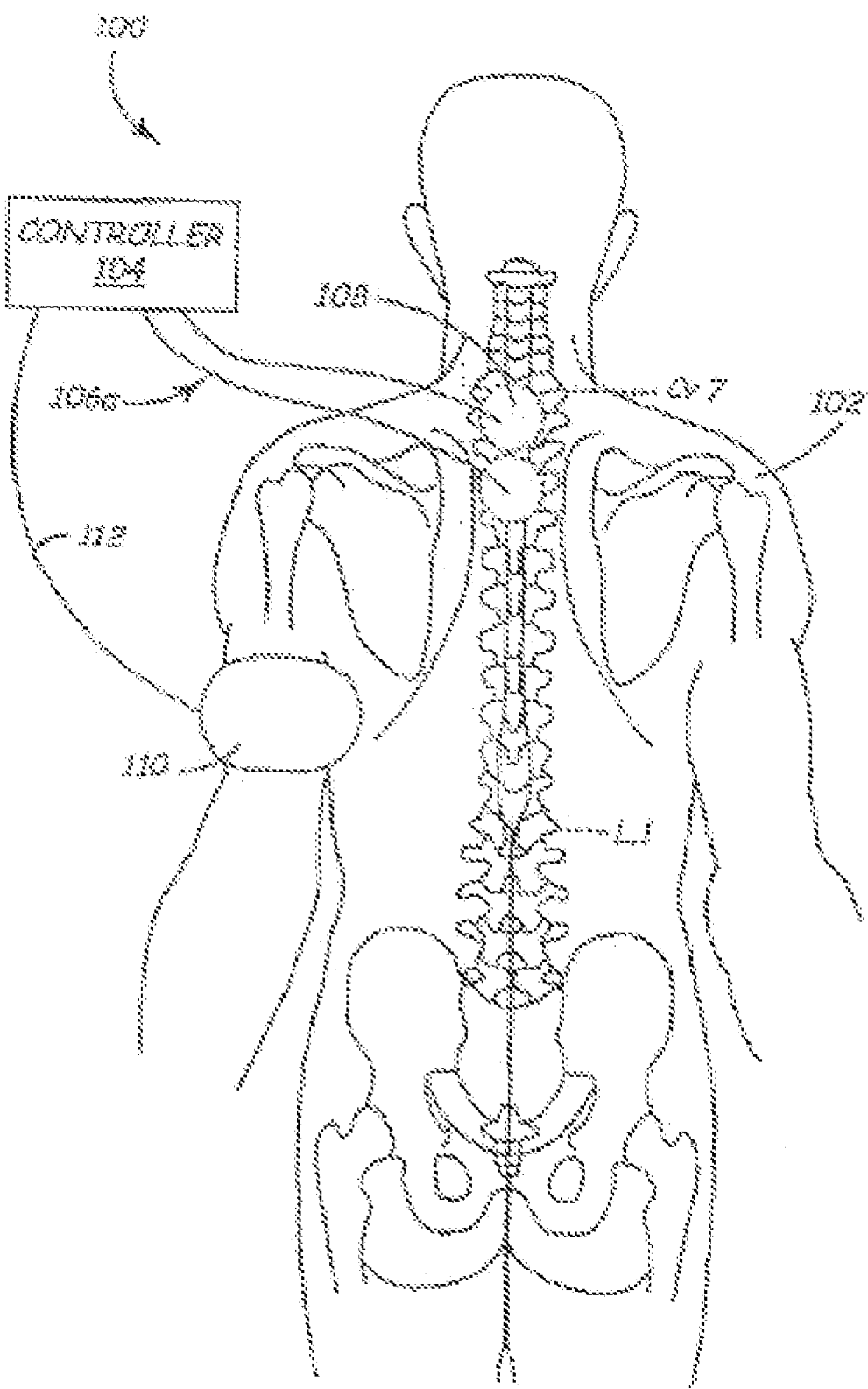
FIG. 1A illustrates a stylized representation of a posterior view of a patient with electrodes positioned thereon.
Figure 1B:
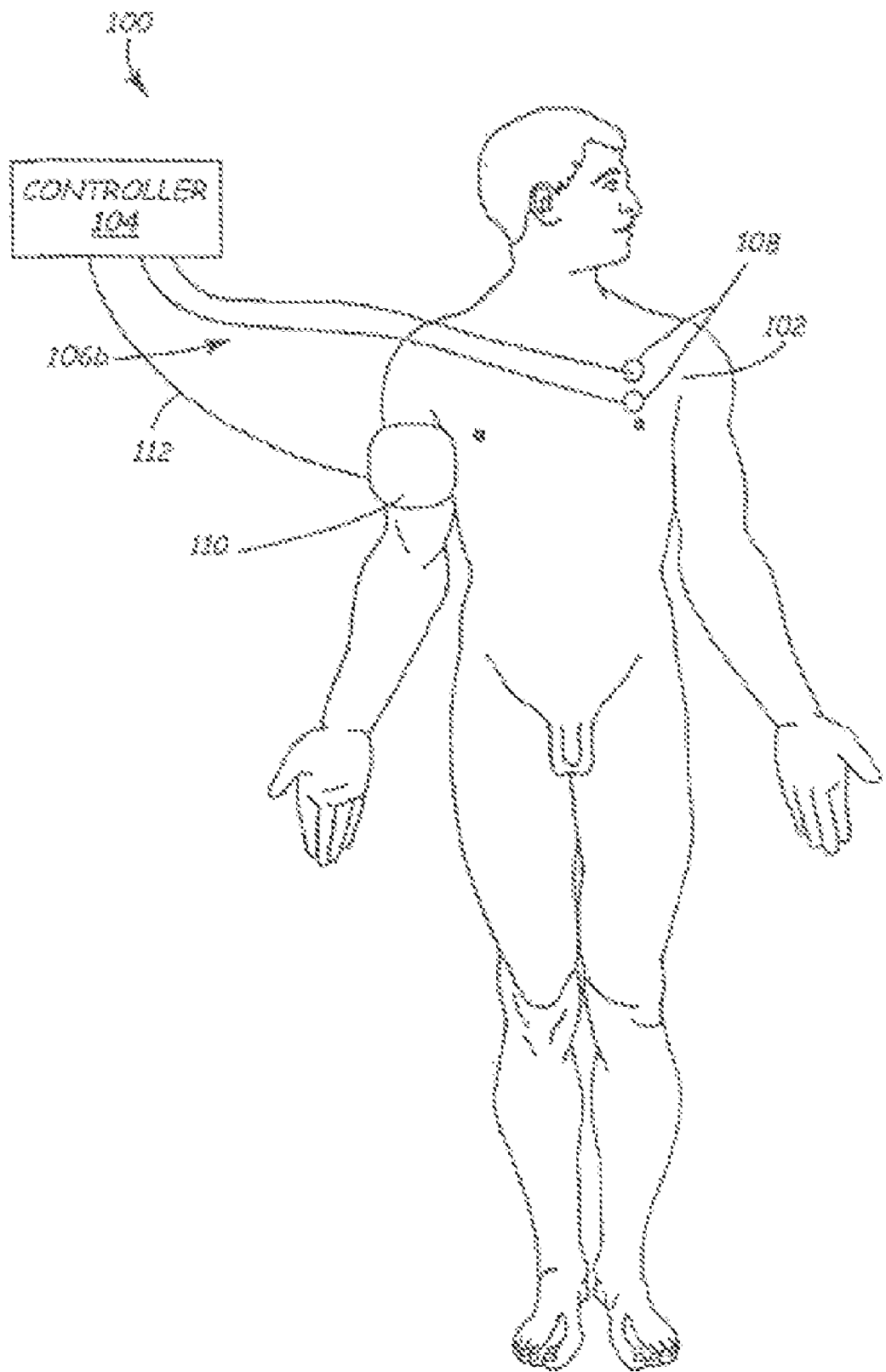
FIG. 1B illustrates a stylized representation of an anterior view of a patient with electrodes positioned thereon.

As shown in FIGS. 1A and 1B, a system 100 may provide stimulation to a patient 102 on or in the spinal cord or the associated dermatomes to regulate the release of hormones. Stimulation may be administered by spinal cord stimulation (SCS), Transcutaenous Electrical Neurological Stimulators (TENS), or subcutaneously. Excitation of sympathetic fibers has been shown to lead to the release of catecholamines from the adrenal medulla and the release of renin from juxtaglomerular cells near glomeruli of the kidneys. High concentrations of catecholamines and renin are associated with the progression of certain cardiovascular diseases or worsening prognosis for patients with certain cardiovascular diseases, such as sudden cardiac death, heart failure, and hypertension. Thus, their suppression can have positive cardiovascular effects in a fashion similar to that seen with cardiovascular drugs such as beta-adrenergic receptor blocking drugs and ACE inhibitors.

Electrical stimulation can also be used to increase the release of calcitonin gene-related peptide (CGRP), a neural peptide, as well as nitric oxide (NO) and vasoactive intestinal peptide (VIP), all of which are known to cause vasodilation. CGRP, specifically, is known to regulate inotropy, chronotropy, microvascular permeability, vascular tone, and angiogenesis, and is known to protect the myocardium against ischemia-reperfusion injury. Thus, stimulating the release of these hormones can have positive cardiovascular effects. Dorsal column stimulation and stimulation of the sacral nerve roots causes inhibition of the sympathetic nervous system, which then leads to the release of CGRP, which in turn stimulates the production of nitric oxide. This effect stimulates blood flow, which may be particularly useful for treating ischemia. Research by Dr. Robert Foreman and Dr. John Groom has shown that spinal cord stimulation in lower thoracic regions can cause significant vasodilation of foot blood vessels by release of CGRP. Am. J. Physiol., Vol. 272, H950-H957 (1997).

Levels of other hormones may also be regulated using the methods and apparatus of this invention. For example, the release of angiotensin I or angiotensin II may be regulated indirectly through the regulation of renin levels and aldosterone and thyroid hormone levels involved in sympathetic activity may be regulated.

As shown in FIGS. 1A and 1B, a system 100 may provide electrical stimulation to a patient 102 adjacent one or more of the locations T1-T12, and C1-C8 or to nerves controlling hormone release to directly or indirectly promote or inhibit release of a desired hormone to regulate the level of the hormone.

A controller 104 is coupled through conventional conductive links 106, such as leads or wires, to one or more electrodes 108 mounted in a region on or in the spinal cord or the associated dermatomes. In a particular embodiment, the one or more electrodes may be mounted in a region on or in the T7-L2 vertebral levels and their associated nerve bundles. The electrodes 108 may take on a variety of forms, including but not limited to surface mounted electrodes, subcutaneous electrodes, and implanted electrodes. All of these types of electrodes, properly placed, may be used to stimulate the spinal cord or associated dermatomes. These electrodes are coupled to the controller 104 to provide electrical stimulation at the desired point.

Stimulating electrodes may be, for example, cuff-type, needle-type, probe-type, transcutaneous, intracutaneous, patch-type, balloon-type, basket-type, umbrella-type, tape-type, screw-type, barb-type, metal, wire, or suction-type electrodes. Surface mounted electrodes may be fixed to the patient 102 via any of a variety of conventional mechanical or chemical mechanisms, or may simply be held in place by friction and gravity. Subcutaneous electrodes are surgically inserted into the patient's body and used to stimulate nearby nerves. Examples of subcutaneous leads include the Pisces® and OnPoint® model leads, commercially available from Medtronic Corporation. Implanted electrodes may simply be subcutaneous electrodes carried on the surface of an implanted medical device, as disclosed in commonly-assigned U.S. Pat. No. 5,292,336, incorporated herein by reference. Alternately, they can be electrically isolated, as disclosed in commonly assigned U.S. Pat. No. 5,331,966, incorporated herein by reference.

In one embodiment, a paddle-type (flat) lead having a surface area between one square cm and 12.7 square cm or more may be used to accomplish subcutaneous stimulation. Such a lead may be formed of an insulative material, with programmable electrodes on one or more of the flat sides of the lead. In this embodiment, the paddle-type lead is between four and ten millimeters wide so that it can readily pass through a twelve-gage needle before it unfolds. A nerve stimulator electrode available from Medtronic Inc. is lead Model 3987 On Point®, with four connects and a polyester mesh skirt for fixation to subcutaneous tissue or muscle fascia. Other Medtronic leads might also be used, including Model 3587A or Model 3998, which have an insulative paddle enlargement, or Model 3487A or Model 3888, which do not. A spinal cord stimulating electrode bearing recording electrodes acting as sensors is another embodiment. This type of electrode is disclosed in U.S. Pat. No. 5,824,021.

For spinal cord simulation, the spinal cord stimulator electrode or electrodes may be placed in any suitable manner for providing stimulation to the spine. The electrodes may be placed invasively or non-invasively. In one embodiment, all or a portion of the electrode is implanted adjacent to the spine, in the epidural space, using Pisces®, Pisces Quad Plus®, and Octad® model leads, commercially available from Medtronic Corporation. Alternatively, all or a portion of the electrode may be implanted adjacent to specific vertebrae.

Implanted electrodes may be placed to stimulate underlying muscles, overlying cutaneous nerves, nerve ganglia, or passing somatic nerves. Electrodes may also be placed to stimulate dermatomes. Dermatomes may be described as a pattern of skin innervated by cutaneous neurons of a certain spinal or cranial nerve, and represent specific regions of nerve reception of sensory impulses. Electrical stimulation may be carried out on more than one area of the spinal cord simultaneously or sequentially.

To use SCS or other nerve stimulation to reduce sympathetic input to the adrenal glands, a number of sites may be stimulated. In one example, SCS is delivered at the T12 vertebral level, over the conus medullaris. When stimulation is delivered at this site the sympathetic center at the tip of the spinal cord may be suppressed. SCS may also be delivered at a higher level, such as the T8 vertebral level, where sympathetic activity to the adrenal glands and the kidneys will be suppressed, thus, inhibiting the release of catecholamines and/or rennin. The T8 vertebral level is also significant, in that this is the spinal level where the L2 nerve roots from the sympathetic chain enter the spinal cord. These are the lowest direct nerve connections from the sympathetic chain to the spinal cord, and stimulation at the L2 level can block most if not all lower back pain. Thus, stimulation at this level may block sympathetically mediated pain or other somatic pain from that level of the body and downward.

A useful method for determining the optimal location for SCS is to determine the spinal level in which paresthesia is felt in the body area nearest the kidneys. Generally, if paresthesia covers the area of pain, there is pain relief and suppression of sympathetic reflexes. Stimulation can also be done at sites outside of the spinal cord itself. The L2 nerve root at the L2 intervertebral foramen and the adjacent areas is one such site. The L2 or other sympathetic ganglia or sympathetic nerves may be stimulated ipsilaterally or bilaterally. Apparatuses and methods for inhibiting peripheral nerves and ganglia are described in U.S. Pat. No. 6,058,331, by King, the disclosure of which is incorporated herein by reference. Alternately, the pelvic or abdominal plexi, or the nerves of the adrenal medulla, may be inhibited through electrical stimulation. Bilateral electrodes are useful for stimulation in this area.

The controller may take the form of an external device or an implantable device. Where the controller is an external device, it may be useful in providing therapeutic signals to a patient who is experiencing an unexpected event. The controller 104 may be programmed for either automatic or manual operation. That is, the controller 104 may have one or more conventional sensors (not shown) of a type capable of sensing hormonal irregularities or disorders such as a decompensation episode of ventricular dysfunction, severe cardiac ischemia, or heart failure. The sensors and control scheme used to detect the hormonal irregularity or other disorder may be conventional, such as those found in implantable defibrillators or pacemakers, when the controller is intended to deal with cardiovascular disorders. Upon detection of a hormonal irregularity or other disorder, the controller 104 may automatically begin treatment of the patient by regulating hormone levels through electrical stimulation. Alternately, the patient or authorized personnel may manually activate the controller 104 to begin regulation of hormone levels through electrical stimulation. Manual activation may be accomplished by any of a variety of mechanisms. For example, where the controller 104 is implanted in the patient, activation may be accomplished by wireless communication or the like.

Figure 1C:
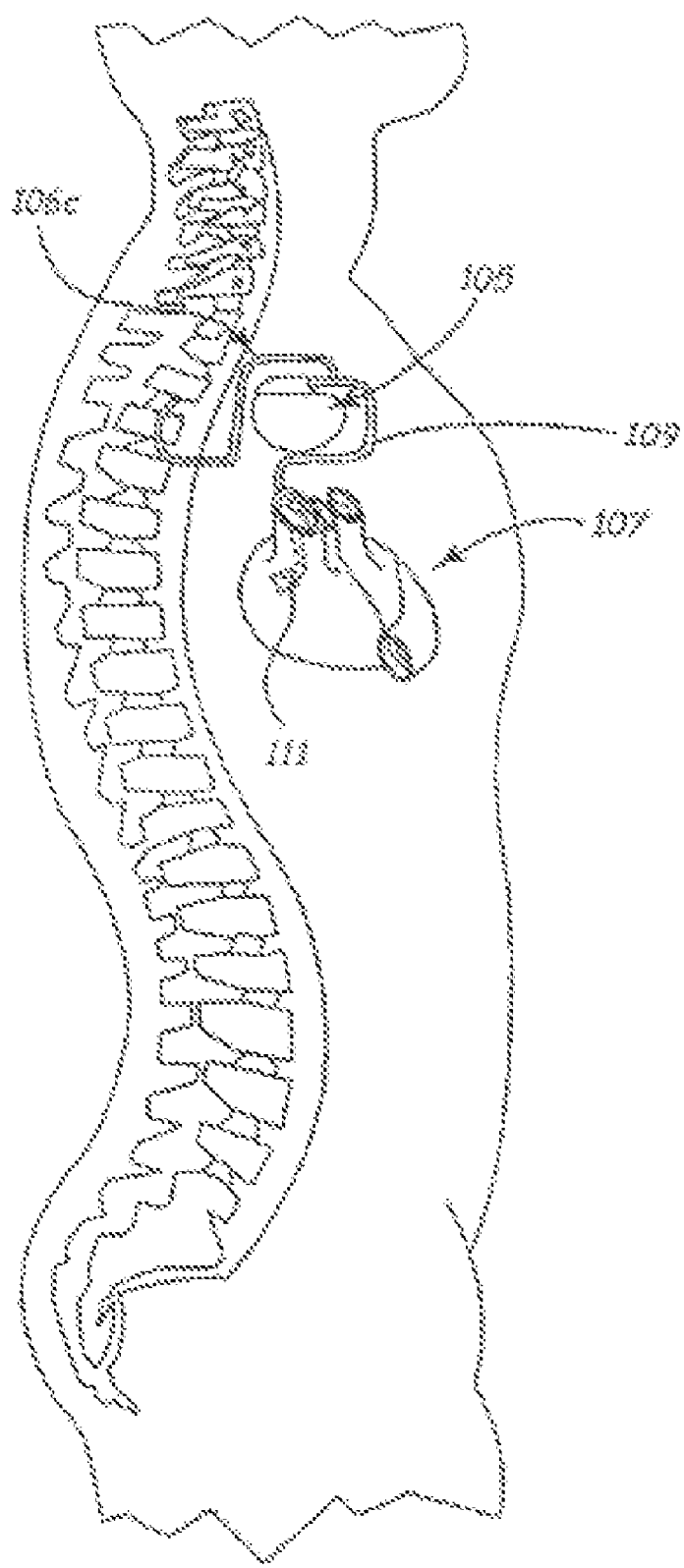
FIG. 1C is a diagram illustrating an implantable stimulation device implanted within a patient.

In those situations in which a patient has a history of physiological disorders, it is generally useful to construct the controller 104 in a housing 105 designed to be implanted within the human body, as shown in FIG. 1C. In this embodiment, implanted lead 106c is employed to deliver electrical stimulation according to the invention. The housing may optionally include a pacing and/or cardioverter/defibrillator stimulation circuit for generating cardiac stimulation signals to the heart 107 using one or more leads, as is known in the art. Leads 109 may also carry one or more physiological sensors 111 for sensing physiological signals, as discussed below. These sensors may be any of the types known in the art for sensing physiological signals, including pressure, oxygen, activity, temperature, and blood flow sensors. Exemplary sensors are disclosed in U.S. Pat. No. 4,903,701, issued to Moore et al., U.S. Pat. No. 5,564,434, issued to Halperin et al., U.S. Pat. No. 4,428,378, issued to Anderson et al., U.S. Pat. No. 5,464,434, issued to Alt or U.S. Pat. No. 5,330,505, issued to Cohen, all incorporated herein by reference in their entireties. The sensors may include externally placed electrodes for measuring ECG signals in a manner known in the art or sensors that externally measure blood chemistry.

Additionally, or in the alternative, the housing may also include a drug delivery device such as a drug pump coupled to a drug delivery catheter that may be used with nerve stimulation to provide combination or synergistic therapy using a biologically active agent alongside electrical stimulation to prevent or ameliorate a detected physiological disorder.

The treatment administered by the controller 104 may take on a variety of different forms. In one embodiment, SCS may be used to regulate the levels or cardiovascular hormones, such as renin, catecholamines, and/or CGRP, in conjunction with another type of therapy, such as one or more types of heart-pacing therapies. For example, an adjustment of the atrial-to-ventricular and ventricular-ventricular timing during atrial-synchronized bi-ventricular pacing (cardiac resynchronization therapy) may be performed at about the same time as SCS in order to further improve the performance and efficiency of the heart.

Additionally, electric stimulation therapy may be administered along with cardiac resynchronization therapy to further improve the cardiac performance and efficiency of the heart. That is, the SCS or other electric stimulation (e.g. TENS, subcutaneous) therapy may be administered shortly before, shortly after, or at the same time as resynchronization or other pacing therapy. For example, hormone regulation by electric stimulation may be administered in conjunction with bradycardia pacing therapy, such as changes in the lower rate limit therapies for increasing cardiac output or pulse pressure and post extra-systolic potentiation pacing or non-excitatory stimulation pacing. Electric stimulation may also be used with therapies for preventing arrhythmias or reducing arrhythmic burden, such as arrhythmia prevention pacing algorithms, consistent atrial or ventricular pacing, and rate stabilization pacing. In particular, one exemplary scheme involves administering the electrical stimulation in conjunction with overdrive RV apical pacing to provide an increased cardiac output in patients with obstructive cardiomyopathies.

In one embodiment, delivery of electrical stimulation for the regulation of hormone levels is modified based on a variety of measurable physiological parameters. As depicted in FIGS. 1A and 1C, representative sensors 110 and/or 111 may be positioned adjacent to or within the body of the patient 102 to sense various physiological conditions that are communicated back to the controller 104 over the leads 112. The measured physiological conditions are used to determine when hormonal regulation is desired and may be used to monitor the conditions as an indication of the patient's response to the therapy being administered by the controller 104. That is, a positive physiological response may be used as an indication that the electrical stimulation suppressing or increasing release of hormones associated with cardiac function is achieving the desired result. The sensed physiological conditions may also be used to adjust the parameters of the electrical stimulation. For example, the controller 104 may measure and record blood pressure. A change in blood pressure may be used in a closed-loop system to adjust delivery of electrical stimulation. For example, if the controller 104 detects that heart rate has increased over time, electrical stimulation may be increased in order to decrease levels of catecholamines, thereby lowering heart rate to desired levels. Where the controller 104 observes a consistent, appropriate heart rate, then the stimulation delivered may be continued at the current rate. On the other hand, where the controller 104 observes a decreasing heart rate, the electrical stimulation may be decreased or electrical stimulation increased at a different site in order to increase the level of catecholamines, thereby increasing heart rate.

Many other parameters may be measured and used as feedback in a closed-loop control system for the regulation of hormone levels by electrical stimulation. Parameters include, but are not limited to cardiovascular parameters, such as pressure-volume (PV) loops, pressure-area (PA) loops, pressure-dimension (PD) loops, diastolic and systolic pressures, estimated pulmonary artery pressure, change in cardiac pulse pressure, pre-ejection timing intervals, heart rate measures (such as rates, intervals, and the like), autonomic indicators (such as sympathetic neurotransmission, hormone levels, and the like), or various other activity or chronology indicators (such as activity, respiratory rate, time of day, and the like). Additionally, because sympathetic activity to the kidneys suppresses urine production, one can monitor urine product as a measure of sympathetic activity.

A more comprehensive, yet still partial, listing of physiological parameters and their associated sensing methods are summarized in Table 1 below. In Table 1, column 1 lists general categories of sensors, column 2 corresponds to a particular physiological parameter that may be monitored, column 3 outlines a corresponding sensor used to monitor the parameter, and column 4 relates to the type of physiological condition or occurrence that may be anticipated using the measurement.

TABLE I

| | Physiological Parameters to be Sensed or Monitored | | |
|---|---|---|---|
| General Modality | Specific Items | Sensing Methods | Corresponds To: |
| Physical Activity | Posture | Gravity direction, accelerometer | Posture |
| | Ambulation/Motion Detector | Piezoelectric Crystal, accelerometer | Motion |

TABLE I-continued

Physiological Parameters to be Sensed or Monitored

| General Modality | Specific Items | Sensing Methods | Corresponds To: |
|---|---|---|---|
| | Minute Ventilation | Impedance | Respiration (rate and volume) |
| | Temperature | Thermistor | Body temperature |
| | Blood changes with activity | $PO_2$, $SAO_2$, pH, Catecholamines, adrenalin | Blood chemistry |
| Cardiac Electrical Activity | Changes in Morphology of Complexes (QRS, T waves) | ECG, Intracardiac Electrogram (EGM), subcutaneous Electrogram (EGM) | Changes in cardiac depolarization or repolarization patterns |
| | Repolarization Alternans, T Wave Alternans, QRS Alternans, ST Segment Alternans | ECG, Intracardiac EGM subcutaneous EGM | Abnormalities on cardiac electrical depolarization, and repolarization |
| | Heart rate & rhythm (NSVT episodes of VT/VF, PVC's heart rate variability | ECG, Intracardiac EGM subcutaneous EGM | Cardiac rhythms, regularity |
| | Changes in AV Interval, AV Interval variability, dynamic responses of AV interval to changes in HR Changes in QT Interval QT Interval variability, Responses of QT Interval to changes in HR | ECG Intracardiac EGM subcutaneous EGM ECG, Intracardiac EGM subcutaneous EGM | Cardiac conduction abnormalities, autonomic and paracrine modulation of same Cardiac repolarization autonomic and paracrine modulations of same |
| Cardiac ischemia | ST Segment changes, Q Wave, QRS magnitude and width | ECG, Intracardiac EGM subcutaneous EGM, blood chemistry (see below) | Myocardial perfusion (balance between supply and demand) |
| Neuro Activity | Cardiac neurons and nerves | Neuronal recordings | Sympathetic neurons and nerves |
| Neutral Activity | EEG | Cortical motor strip | Global neutral activity |
| | EMG | Paraspinal muscles | Increases indicate cardiac stress |
| | | Other muscles | |
| | Certain nerves | Sympathetic | Increases indicate heart stress |
| | | Parasympathetic | Increases indicate relaxation |
| | | Somatic | Correlates to activity |
| Autonomic Activity | Heart rate variability Baroreflex sensitivity, HR, BP and respiration coupling relationships, Heart rate turbulence | ECG, intracardiac or subcutaneous EGM, Pressure transducer, Lung Impedance | Autonomic tone, baroreflex, respiratory Sinus arrhythmia |
| Hemodynamic Parameters | Arterial or Venous Pressure | Pressure transducer | Systolic Diastolic and Pulse pressure; central venous pressure |
| | Cardiac chamber pressures | Pressure transducer | Developed pressures, peak systolic, diastolic pressures, dP/dt |
| | Cardiac mechanical activity | Accelerometer, sonomicrometer crystals | Tissue displacement, coordination, contraction |
| Blood Chemistry (central arterial and local tissue | $PO_2$ $SAO_2$ | Oximetry, $O_2$ Probe | Related to cardiac performance |
| | Glucose | Oximetry | Indicator of Myocardial Metabolism |

TABLE I-continued

Physiological Parameters to be Sensed or Monitored

| General Modality | Specific Items | Sensing Methods | Corresponds To: |
|---|---|---|---|
| and differences between these) | Lactate | Oximetry | Indicators of Myocardial Metabolism |
| | PC $O_2$ | C $O_2$ Probe | Related to cardiac performance |
| | pH | pH Probe | Abnormalities may indicate myocardial electrical instability |
| | Troponin | Molecular Probe | Indicators of Myocardial Ischemia |
| | CKMB | Molecular Probe | Indicators of Myocardial Ischemia |
| | Electrolytes | Molecular Probe | Abnormalities may indicate myocardial electrical instability |
| | Drug levels | Molecular Probe | As indicators of level of protection provided by drug (e.g. antiarrhythmics) |
| | Catecholamines | Molecular Probe | Autonomic Activity/Tone |
| | NO or precursors | Molecular Probe | Related to cardiac injury |
| | Endogenous opiates | Molecular Probe | Autonomic Activity/Tone |
| Time of Day | Clock/Date | Track because activity and risk vary during day or year | |

Those skilled in the art will appreciate that any one of a wide variety of measurable physiological parameters may be monitored and used to implement the closed-loop adaptive controller described herein. An exemplary controller, used in a closed-loop feedback control for the treatment of peripheral vascular disease, is described in U.S. Pat. No. 6,058,331. Any one or more of the sensing devices listed in Table 1, and/or other physiological sensors, may be employed without departing from the scope of the present invention. Note also that it is particularly desirable to monitor urine production for the present invention, as total suppression of sympathetic activity leading to the adrenal medulla may result in a cessation of urine production. If this results, the level of electrical stimulation should be decreased and/or only administered when catecholamine levels are too high or the heart is becoming stressed.

Any combination of the foregoing may be used to determine the timing, waveforms, and amplitude of the electrical stimulation delivered to the electrodes 108. Those skilled in the art will appreciate that the illustrated, representative sensor 110 may take on any of a variety of forms, depending on the physiological parameters being sensed. Generally, these feedback parameters may be detected and used to control certain parameters of the stimulation, such as the magnitude, duration, duty cycle, and frequency. In one embodiment, the present invention may be implemented by providing pulses to the electrodes having amplitudes of 0.1 to 20 volts, pulse widths varying from 60 to 1000 microseconds, and repetition rates varying from 5 to 185 Hz or more. Those skilled in the art will appreciate that these ranges may vary depending upon the particular application. For example, repetition rates between 5 and 100 Hz are generally used to excite neurons, and above 100 Hz to inhibit neurons. SCS may use the lower frequency range to responsively inhibit sympathetic outflow. Stimulation of the sympathetic neuronal ganglia or sympathetic neurons may use the higher frequency range to directly inhibit sympathetic outflow. With greater stimulation parameters (increased magnitude, increased frequency, increased duty cycle, and/or increased pulse durations) a withdrawal of sympathetic activity will result, decreasing the levels of catecholamines. This effect recreates the effect of beta-blockers, without requiring the administration of drugs. The "beta-blocker-like" effect results in decreased contractility, alteration in blood flow (including increase in coronary supply), improved cardioprotection, and decreased workload or demand. The appropriate stimulation pulses are generated based on the algorithms shown in FIGS. 4A-4D that read the sensor signal(s) and make the appropriate analysis.

Pre-set parameters may also be used in order to provide an appropriate response to physiological changes reported by the sensors 110 and/or 111. For example, if the patient is having a significant tonic increase in blood pressure without an accompanying increase in physical activity "more strenuous" stimulation parameters (e.g. increased magnitude, increased pulse width, and increased frequency) may be used to provide the greatest amount of protection and local withdrawal of sympathetic activity. For a less severe event, such as an elevation in end diastolic pressure, "less strenuous" stimulation parameters may be used to provide an incremental adjustment to the cardiac function.

Figure 2:
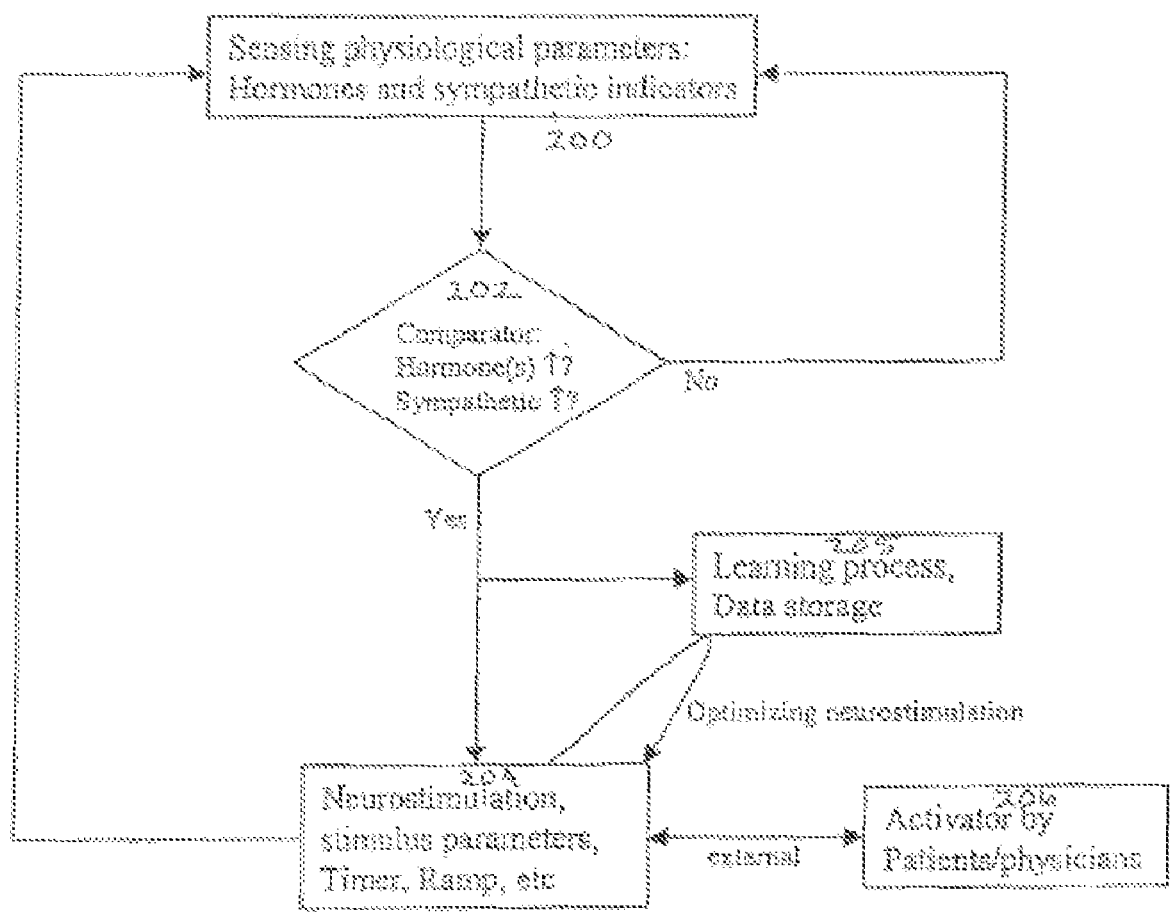
FIG. 2 illustrates a stylized flowchart of a control routine that may be performed by the controller of FIG. 1.

The overall operation of a device of the invention is illustrated in the flowchart depicted in FIG. 2. Those skilled in the art will appreciate that the flowchart illustrated herein may be used to represent either software that may be executed by a processor or hardware configured to operate to perform the functions set forth in the flowchart. The process depicted in FIG. 2 begins at block 200 with the assumption that the measurement of at least one physiological parameter indicates that the level of one or more hormones should be increased or decreased. For example, a patient's blood pressure may rise and stay at a higher than normal level without changes in the patient's physical activity or other normal causes that may result in increased blood pressure, for example. It is known that an increase in the level of noradrenaline, a catecholamine, and/or renin, the precursor of angiotensin II, causes an increase in blood pressure. Therefore, stimulation of appropriate neural tissue, such as the spinal cord will inhibit the release of one or both of those hormones and the patient's blood pressure will decrease.

FIG. 2 depicts a generalized mode of closed loop operation. Block 200 represents the action of the sensors, such as those shown as 110 and 111 in FIG. 1A or 1C, which obtain information on physiological parameters and transmit that information to the controller where the information is accepted and processed. The processor in block 202 compares the measured parameters to the corresponding desired ranges. These parameters may be levels of sympathetic neurotransmission, hormone levels, or various other parameters. If the parameters are within the desired range, the software logic returns to block 200 where further sensor information is obtained and transmitted, and the process repeats. If, however, the measured parameters fall outside the desired range, such as if the sympathetic activity or hormone levels are too high, then a processor at block 202 sends a signal to an electrode at block 204 to cause stimulation of neural tissue at a desired site. The stimulus parameters may vary depending on the information regarding the physiological parameters sensed by the sensors. The neurostimulation activity orchestrated by block 204 may also be controlled directly through activation by the patient and/or physician, as shown by block 206. Thereafter, the process returns to block 200 to repeat, based on the current information from the sensors.

It should be appreciated that, due to physiological differences between patients and the differences between the metabolic degradation rate of various hormones and in their biological activity, stimulation of neural tissues and appropriate adjustments to the stimulation parameters may not produce an immediate, precise change in all patients. Rather, it is anticipated that each patient will respond substantially uniquely to neurostimulation of tissue and to variations in the stimulation parameters. Thus, it may be useful to add a learning process 205 to the operation of the feedback arrangement just described. For example, it may be useful to control the rate at which the stimulation parameters are allowed to change, or to develop a histogram for a particular patient. The learning system 205 could include the ability to record parameters associated with the delivered electrical stimulation such as pulse widths, frequencies, duty cycles, and time-varying patterns. These parameters and the patient's response may be recorded in the memory, for example. Based on patient response, the efficacy of electrical stimulation to inhibit or increase the release of one or more hormones can be evaluated so that the delivery of electrical stimulation can be adjusted to improve the physiological response. This "learned" capability allows the system to optimize delivery of electrical stimulation based on the results of previous efforts, so that treatment is automatically is adjusted and tailored to the needs of individual patients. Furthermore, it may in some instances be useful to tailor therapy for a given patient based on prior learning obtained for a different patient with a similar background and physiology. It may also be useful for the system to be able to recognize and respond appropriately to multiple types of events, differing in, for example, severity, rate of onset, time of day or occurrence, patient activity levels, etc., and to treat these events with a uniquely tailored set of treatment parameters.

Figure 3:
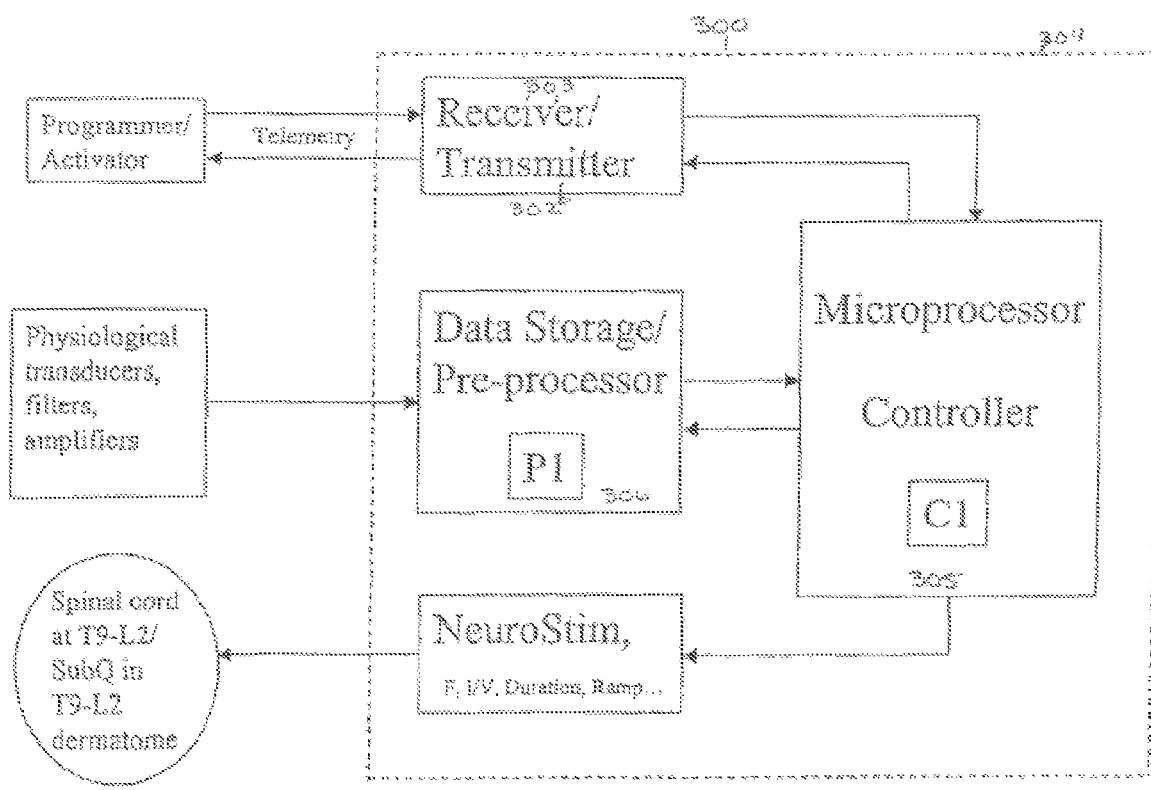
FIG. 3 is a diagram illustrating one embodiment of the instant invention.

FIG. 3 illustrates a block diagram of one embodiment of a system of the invention 300. Generally, a controller 304 is comprised of one or more transmitters 302 and receivers 303 that are involved in sensing information from sensors (not shown) or a programmer or activator 304. A microprocessor 305, operating under software or hardware control may instruct the electrodes to produce a stimulating signal having a set of pre-selected parameters such as frequency, duty cycle, duration, waveform shape, amplitude, voltage, and magnitude.

The receivers 303 are generally responsible for receiving signals from the sensors, and processing those signals into a form, such as a digital format, which may be analyzed by the controller 304 and/or stored in a data storage and/or pre-processor area 306, such as a dynamic random access memory (DRAM). The data storage 306 may also store software, which is used to control the operation of the processor 304.

In one embodiment, signals stored in data storage 306 may be transferred via a transmitter 302, such as a telemetry circuit, to an external device, such as a programmer. These signals may be stored in the external device, or transferred via a network (not shown) to a remote system (not shown), which may be a repository or some other remote database. Networks useful with the system of the invention, include without limitation, an intranet, internet system such as the world-wide web, or any other type of communication link.

As noted above, controller 304 may further include a drug delivery device (not shown). Exemplary implantable drug delivery systems that may be adapted to deliver biologically active agents in conjunction with hormone regulation through electrical stimulation are disclosed in U.S. Pat. No. 5,607,418, issued to Arzbaecher, U.S. Pat. No. 5,220,917, issued to Cammilli, U.S. Pat. No. 4,146,029, issued to Ellinwood, and U.S. Pat. No. 5,330,505, issued to Cohen.

Figure 4A:
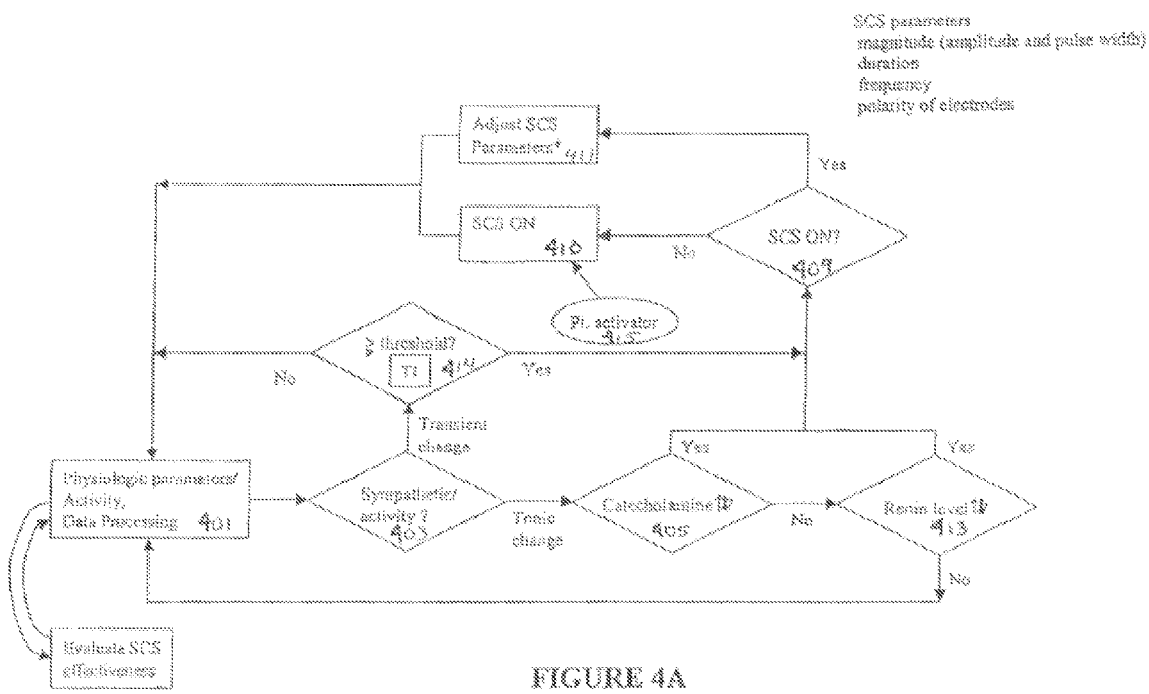
FIGS. 4A-4D are flowcharts depicting control routines that may be performed by a controller of the instant invention.

FIG. 4A is a flowchart illustrating one embodiment of the controller of the present invention. Sensors in block 401 sense various physiologic parameters of a patient, including physical activity levels. A determination is made as to whether an increase or decrease in sympathetic indicators or in physical activity indicators in the patient as shown in block 403, such as may be seen in a cardiovascular disorder such as ventricular dysfunction, heart failure, or an imbalance of autonomic tone or the neuroendocrine system. This determination is based on the measured physiological parameters that may include detection of physical activity, heart rate, urine levels, blood pressure and the like. Other parameters may be measured in a manner such as those discussed above.

If a tonic change in sympathetic and/or activity indicators is detected then a determination is made as to whether there is a change in catecholamine levels as shown in block 405. If yes, then the controller will determine whether the neurostimulating electrode is currently stimulating neural tissue, such as the spinal cord, as shown in block 409. If there is no stimulation, stimulation to the appropriate site of the spinal cord to modulate catecholamine release will begin as shown in 410. The physiologic parameters will continue to be measured as shown in block 401 and if those measurements indicate a continued change in sympathetic and/or activity indicators once the stimulation is occurring then the stimulus parameters will be adjusted as shown at 411 to increase or decrease stimulation and promote or inhibit release of a desired hormone until the sympathetic and/or activity indicators return to the predetermined level. For example, the stimulation may be increased if catecholamine levels are increased or sympathetic indicators are increased and decreased if the hormone activity and/or sympathetic activity indicators show an unusual decrease. Also, in some instances it may be desirable to change the location of the stimulation, which can be accomplished in one embodiment by changing the polarity of electrodes. The stimulus parameters include, without limitation, magnitude (amplitude and pulse width), duration, duty cycle, frequency, and polarity of electrodes. If continued change in the sympathetic and/or activity indicators is no longer present, or if one or more physiologic parameter measurement indicates that the release of catecholamines has been sufficiently inhibited or increased, electrical stimulation will be deactivated. Deactivation may involve hysteresis, so the stimulation may be terminated gradually over a predetermined period of time.

In FIG. 4A, if there is a tonic change in sympathetic and/or activity indicators and the concentration of catecholamine has not changed, then a determination will be made as to whether the concentration of renin has changed. If no, then the device will continue monitoring the physiologic parameters. If the level of renin is changed as shown in 413, a determination will be made as to whether stimulation of the spinal cord or associated dermatomes is occurring at block 409. If not, the stimulation will be initiated as shown in block 410. If it is occurring, the controller will adjust the stimulus parameters as shown in block 411 until the level of renin is regulated to a desired level.

If only a transient change in sympathetic and/or activity indicators is detected, then as shown in block 414, the measurements of the physiologic parameters are compared to a predetermined threshold value. If the measured parameter values are either greater or less than a threshold value a determination may be made as to whether the stimulation should be activated.

In another embodiment, the spinal cord stimulation may be activated in an open loop format by the patient and/or physician as shown in circle 415. Rather than activating the system when a change in sympathetic and/or activity indicators is detected, the system may include a means for notifying the patient that such a change has occurred and the patient may choose to activate the stimulation. This option may be particularly appropriate for a patient who is involved in an activity that he or she knows should change the sympathetic and/or activity indicators and such change is desired by the patient. Optionally, the physician may program the device to stimulate certain neural tissues at predetermined intervals to maintain hormone levels at a certain concentration.

As described above, the controller may include a data storage/data processing means such as shown in block 401, which may store data regarding the effects of electrical stimulation and which may be used as a learning means to optimize the performance of the system.

Figure 4B:
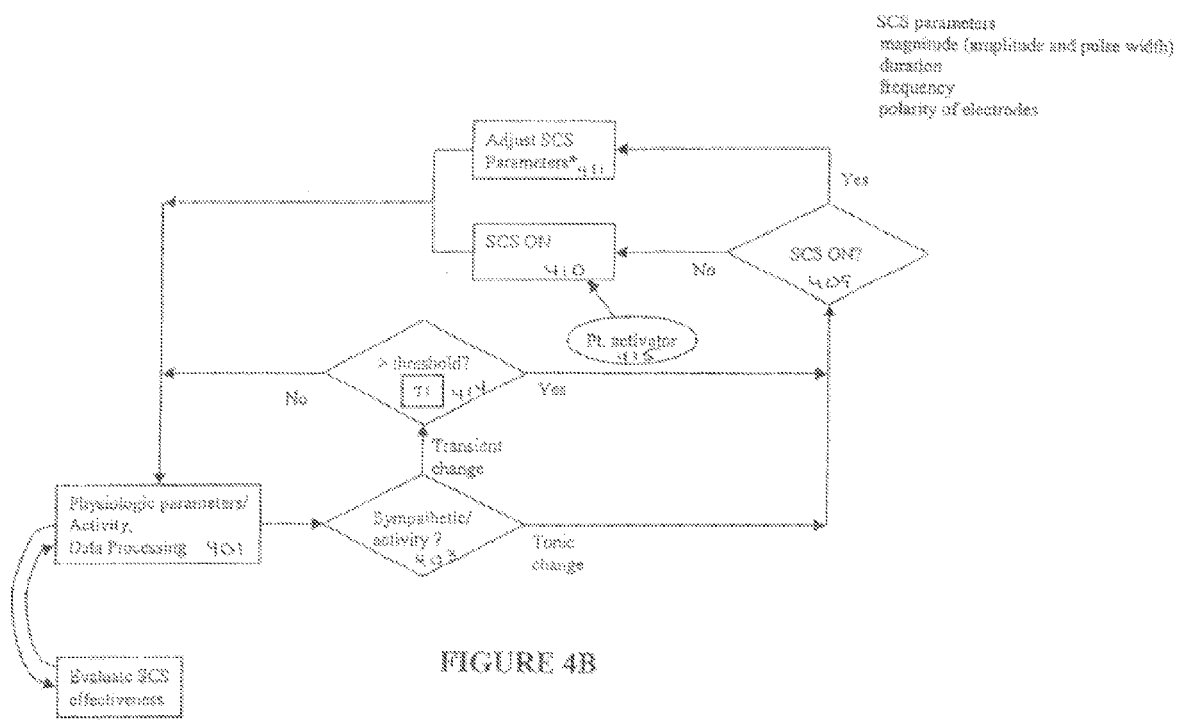
Figure 4C:
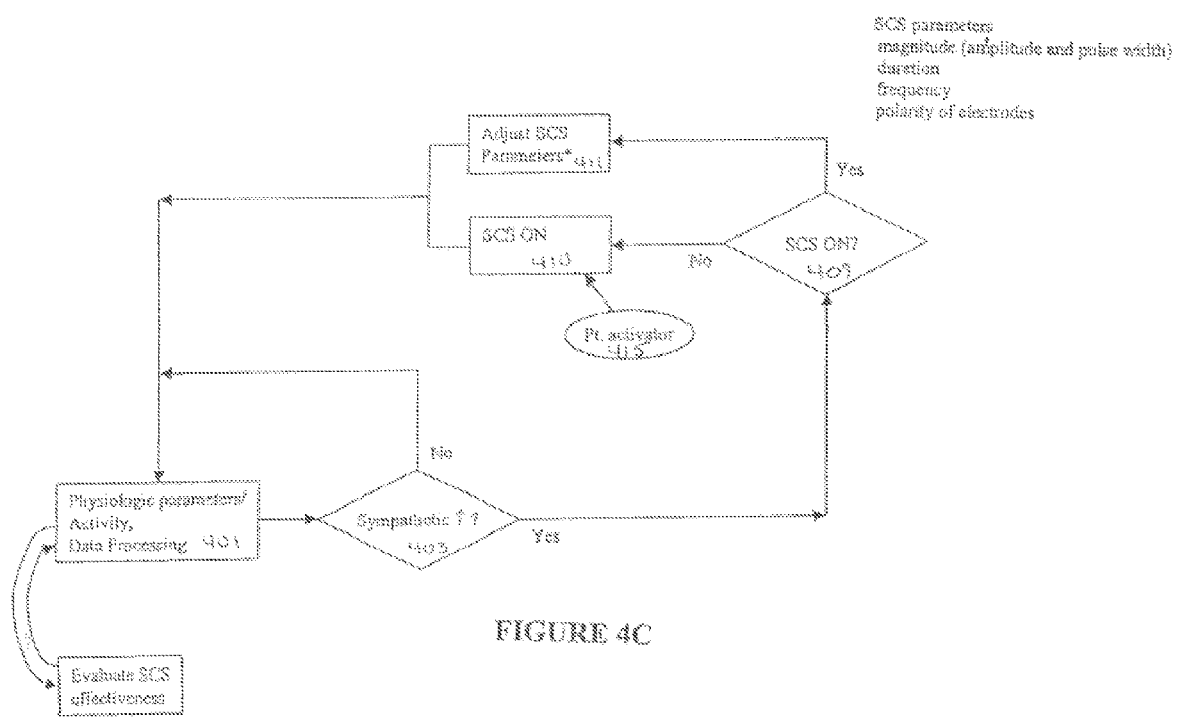
Figure 4D:
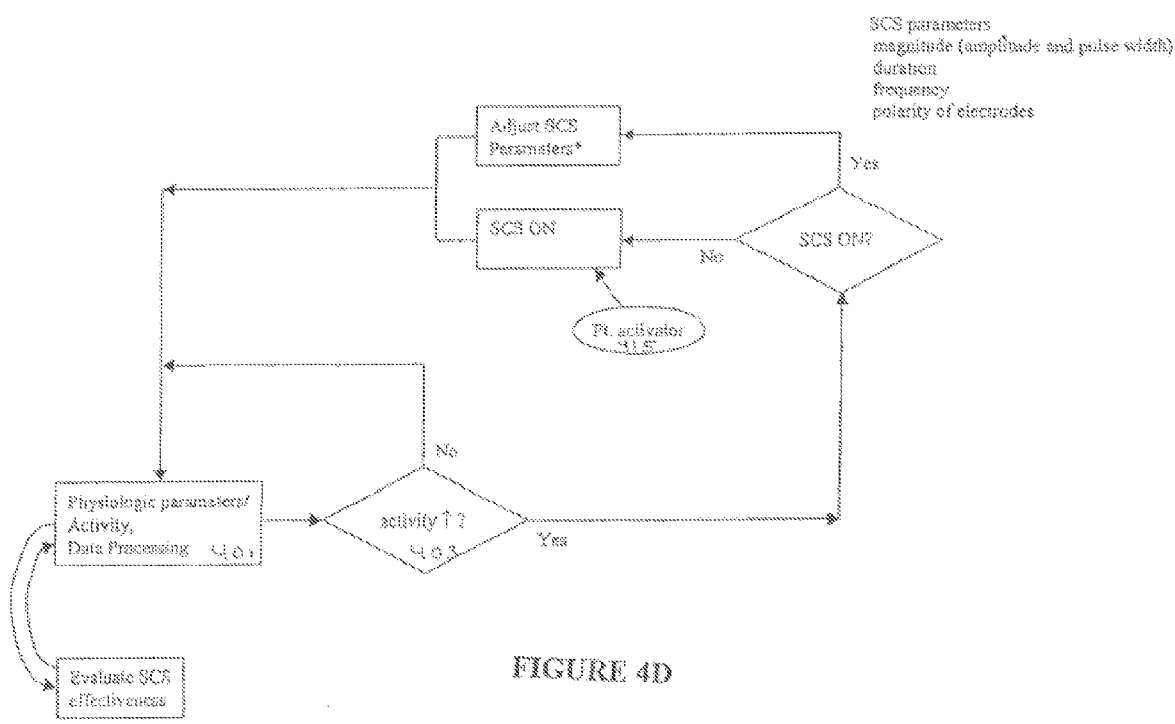
Figure 8:
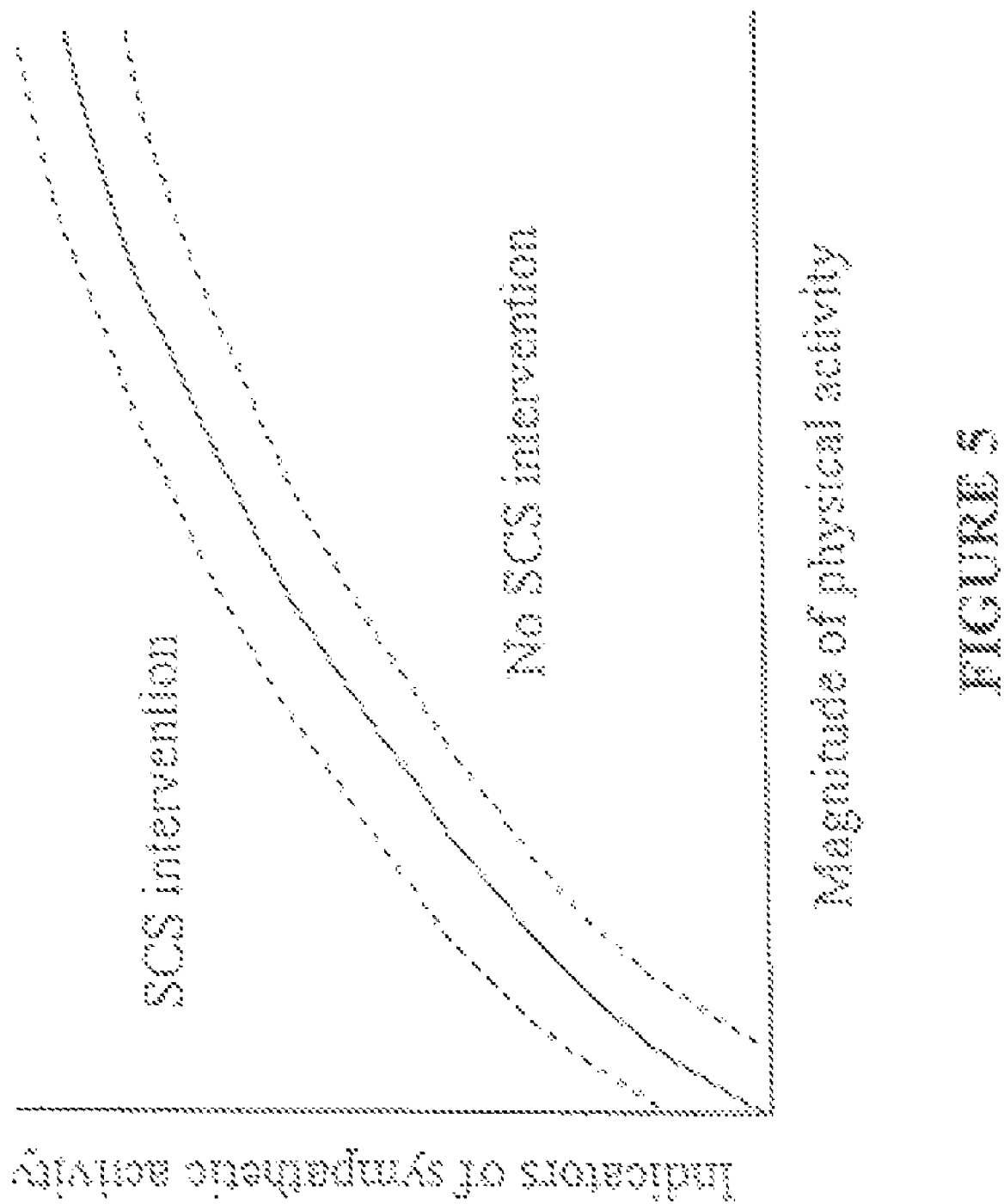

FIG. 4B-4D are flowcharts each illustrating an embodiment of the controller of the present invention. Sensors in block 401 sense various physiologic parameters of a patient, including sympathetic and activity indicators. As shown in FIG. 4B, the process described above is implemented, without any determination being made regarding the levels of catecholamines and/or renin. Other hormones influence sympathetic and activity indicators and a change in these indicators alone will signal the need for stimulation of neural tissue to modulate the release of such hormones. In addition to changing the stimulus parameters, in certain patients, multiple stimulating electrodes may be used located at different sites in the spinal cord and/or on the dermatomes associated therewith. Stimulating certain neural tissue may result in the increase or decrease of the release of one hormone, while stimulating other neural tissues will result in the increase or decrease of another hormone. The controller may evaluate the effectiveness of stimulating each location independently for a particular patient and a particular type of change in sympathetic and/or activity indicators. In some cases, the release of two or more hormones may be modulated by simultaneously or sequentially stimulating neural tissues at desired locations.

As shown in FIG. 4C, controller 104 may be adapted to only measure changes in sympathetic activity indicators and the associated hormone levels and for any change the process of activating or adjusting stimulation will commence and the stimulation will continue until the appropriate physiologic and/or activity parameter measurements are observed indicating that the concentration level of one or more hormones in the patient's body has been appropriately regulated.

As shown in FIG. 4D, controller 104 may be adapted to only measure changes in physical activity indicators and the level of one or more hormones associated therewith and for any change the process of activating or adjusting stimulation will commence. The stimulation will continue until the appropriate physiologic and/or activity parameter measurements are observed indicating that the concentration level of one or more hormones in the patient's body has been appropriately regulated.

FIG. 5 is a graph illustrating how controller 104 monitors sympathetic excitation indicators and physical activity indicators to identify the threshold value T1 shown in 4A. T1 is the mismatch value. Since some increase in sympathetic activity indicators associated with an increase in physical activity is expected, spinal cord stimulation or other neural stimulation to modulate the release of one or more hormones will not be necessary for certain amounts of increase in sympathetic activity indicators. However, at some level as shown in FIG. 5, in some patients the increase in sympathetic activity indicators will exceed the amount of increase expected as a result of the increase in physical activity.

From the foregoing discussion, one skilled in the art will appreciate that the current apparatus and method for electrically stimulating the release of hormones, including cardiovascular hormones, to treat a variety of conditions, without the side effects and other problems of currently existing hormone-regulating drugs, including the issue of patient compliance.

The particular embodiments disclosed above are illustrative only, as the invention may be modified and practiced in different but equivalent manners apparent to those skilled in the art having the benefit of the teachings provided herein. Furthermore, no limitations are intended with respect to the details of construction or the design shown herein, other than as described in the claims below. It is therefore evident that the particular embodiments disclose above may be altered or modified and that all such variations are considered to be within the scope and spirit of the present invention.

All patents and publications referenced herein are hereby incorporated by reference in their entireties. It will be understood that certain of the above-described structures, functions and operations of the above-described preferred embodiments are not necessary to practice the present invention and are included in the description simply for completeness of an exemplary embodiment or embodiments. In addition, it will be understood that specifically structures, functions and operations set forth in the above-referenced patents can be practiced in conjunction with the present invention, but they are not essential to its practice. It is therefore to be understood that within the scope of the appended claims, the invention may be practiced otherwise than as specifically described without actually departing from the spirit and scope of the present invention.

The invention claimed is:

1. A device for regulating hormone levels through electrical stimulation comprising:
   means for sensing at least one physiologic parameter of a patient, wherein said at least one physiologic parameter directly or indirectly indicates a current hormonal imbalance condition, said means for sensing comprising one of: at least one spinal cord stimulating electrode bearing recording-type electrodes, a pressure sensor, an oxygen sensor, an activity sensor, a temperature sensor, a blood flow sensor;
   means for providing stimulation to a portion of neural tissue of the patient in at least one predetermined site; and
   means for controlling the stimulation means to provide stimulation to one of inhibit and increase release of a hormone when the at least one physiologic parameter indicates the hormonal imbalance condition, and wherein said means for controlling operates to at least partially alleviate said the hormonal imbalance condition, and wherein said hormone is selected from the group consisting of: adrenaline, noradrenaline, and a rennin,
   wherein the predetermined site consists of one of: a portion of the spinal cord at levels T7-L2, a bundle of neural fibers within a region of the T7-L2 dermatomes, a volume of neural tissue nearest the kidneys, a neuronal ganglia.

2. A device for regulating hormone levels through electrical stimulation comprising:
   a sensor adapted to detect at least one physiologic parameter relating to a hormonal imbalance condition of a patient, wherein said sensor sensing comprises one of: at least one spinal cord stimulating electrode bearing recording-type electrodes, a pressure sensor, an oxygen sensor, an activity sensor, a temperature sensor, a blood flow sensor;
   at least one electrode adapted to be positionable at a region adjacent a portion of neural tissue of the patient;
   a controller adapted to generate electrical stimulation by the at least one electrode to be applied to the portion of neural tissue adjacent the at least one electrode to increase or inhibit release of a hormone to at least partially alleviate said hormonal imbalance condition, wherein at least one parameter of the electrical stimulation is controlled as a function of the sensed physiologic parameter, and wherein said hormone is selected from the group consisting of: adrenaline, noradrenaline, and rennin.

3. A device according to claim 2, wherein the electrode is positionable for stimulating one of: a portion of a spinal cord, a plurality of neural fibers near a region of the T7-L2 dermatome, a portion of neural tissue nearest a kidney of the patient.

4. A device according to claim 3, wherein the at least one electrode is adapted for stimulating the spinal cord in the T7-L2 vertebrae or in the associated dermatomes.

5. A device according to claim 2, wherein the sensor is adapted to detect concentrations of the hormone and at least one indicator of sympathetic tone.

6. A device according to claim 2, wherein the sensor is adapted to detect concentrations of hormones selected from the group consisting of a renin, an angiotensin II, an aldosterone, a thyroid hormone, and a calcitonin gene-related peptide.

7. A system for regulating a hormone level in a patient comprising:
   at least one electrode adapted to stimulate neural tissue in a patient's body in at least one predetermined site to regulate a hormone level if the patient's body via electrical stimulation therapy;
   at least one sensor to measure and provide information on at least one physiologic parameter related to the hormone level, wherein said sensor comprises at least one of: at least one spinal cord stimulating electrode bearing recording-type electrodes, a pressure sensor, an oxygen sensor, an activity sensor, a temperature sensor, a blood flow sensor; and
   a controller coupled to the sensor and the at least one electrode to control at least one parameter of the electrical stimulation therapy based on information provided by the sensor and to increase or inhibit the release of the hormone to regulate the hormone level, and wherein said hormone is selected from the group consisting of: adrenaline, noradrenaline, and a renin.

8. The system of claim 7, wherein the controller includes a manual activation mechanism.

9. The system of claim 7, wherein the controller includes means for initiating the electrical stimulation therapy in response to the at least one physiologic parameter measured by the sensor.

10. The system of claim 7, wherein the at least one physiologic parameter is selected from the group consisting of one of a sympathetic and a parasympathetic indicator, a hemodynamic function indicator, and a physical activity indicator.

11. The system of claim 7, wherein the at least one physiologic parameter is the concentration of one or more hormones selected from the group consisting of a renin, an angiotensin I, an angiotensin II, an aldosterone, a thyroid hormone, and a calcitonin gene-related peptide.

12. The system of claim 7, wherein the at least one physiologic parameter is a sympathetic or parasympathetic indicator selected from the group consisting of heart rate, blood pressure, urine production, QT interval, atrioventricular interval, respiration and baroreflex sensitivity.

13. The system of claim 7, wherein the at least one physiologic parameter is a hemodynamic function indicator selected from the group consisting of blood pressure, cardiac output, contractility, and intracardiac pressure.

14. The system of claim 7, wherein the electrode stimulates one of a portion of a spinal cord and a dermatome associated with the spinal cord.

15. The system of claim 7, wherein the electrode is adapted to stimulate a plurality of sympathetic system neurons intrinsic to blood vessels or organs.

16. The system of claim 7, wherein the at least one electrode is adapted to be positioned external to the patient's body.

17. The system of claim 7, wherein the at least one electrode is adapted to be positioned subcutaneously within a portion of the patient's body.

18. The system of claim 7, wherein the at least one electrode is adapted to be implanted within the patient's body.

19. The system of claim 7, wherein the at least one electrode is adapted to be positioned on or in the T7-L2 vertebrae or dermatomes associated therewith.

20. The system of claim 7, wherein the controller includes a microprocessor.

* * * * *